United States Patent [19]

Sharma

[11] Patent Number: 4,621,617

[45] Date of Patent: Nov. 11, 1986

[54] ELECTRO-MAGNETICALLY CONTROLLED ARTIFICIAL HEART DEVICE FOR COMPRESSING CARDIAC MUSCLE

[76] Inventor: Devendra N. Sharma, 22 Carroll House Barrie Estate, Gloucester Terrace, London W2 3PR, United Kingdom

[21] Appl. No.: 383,618

[22] Filed: Jun. 1, 1982

[30] Foreign Application Priority Data

| Jun. 29, 1981 | [GB] | United Kingdom | 8119920 |
| Jun. 29, 1981 | [GB] | United Kingdom | 8200231 |
| Jun. 29, 1981 | [GB] | United Kingdom | 8200974 |

[51] Int. Cl.$^4$ .................. A61M 1/10; A61H 1/02; A61F 2/22
[52] U.S. Cl. .................. 128/1 D; 128/25 R; 128/DIG. 3; 623/3
[58] Field of Search ............ 128/1 D, 1.5, 24 R, 128/25, 44, 64, DIG. 3; 3/1.7; 623/3

[56] References Cited

U.S. PATENT DOCUMENTS

| 3,513,836 | 5/1970 | Sausse | 128/64 |
| 3,733,616 | 5/1973 | Willis, Jr. | 3/1.7 |
| 3,771,173 | 11/1973 | Lamb, Jr. | 623/3 |
| 4,014,318 | 3/1977 | Dockum et al. | 128/1 D |
| 4,192,293 | 3/1980 | Ascrican | 128/1 D |
| 4,302,854 | 12/1981 | Runge | 623/3 |

Primary Examiner—Ronald L. Frinks
Attorney, Agent, or Firm—Holman & Stern

[57] ABSTRACT

An artificial heart or heart strengthening device to simulate the natural heart pulsation of mammals by electromagnetic means which may operate alone or in conjunction with the natural heart.

5 Claims, 10 Drawing Figures

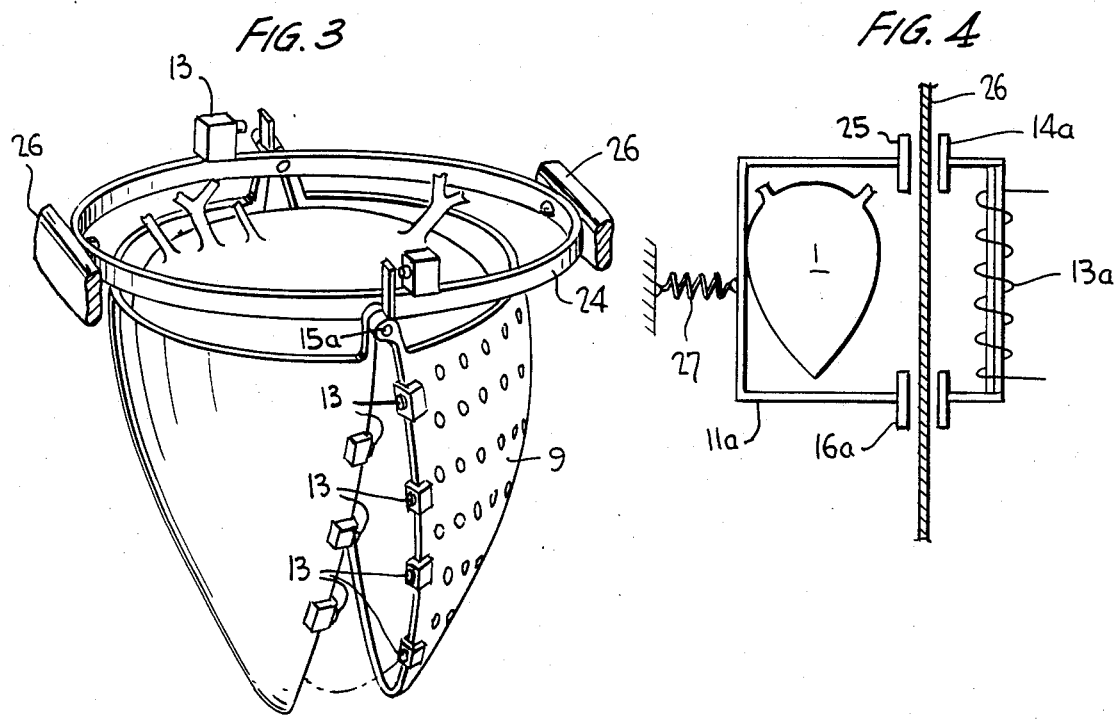
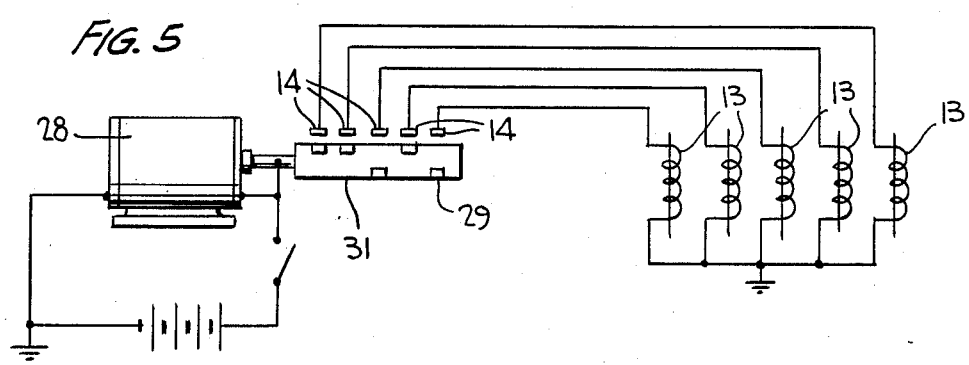
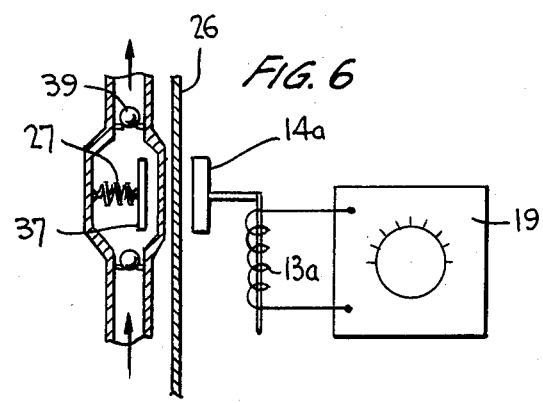

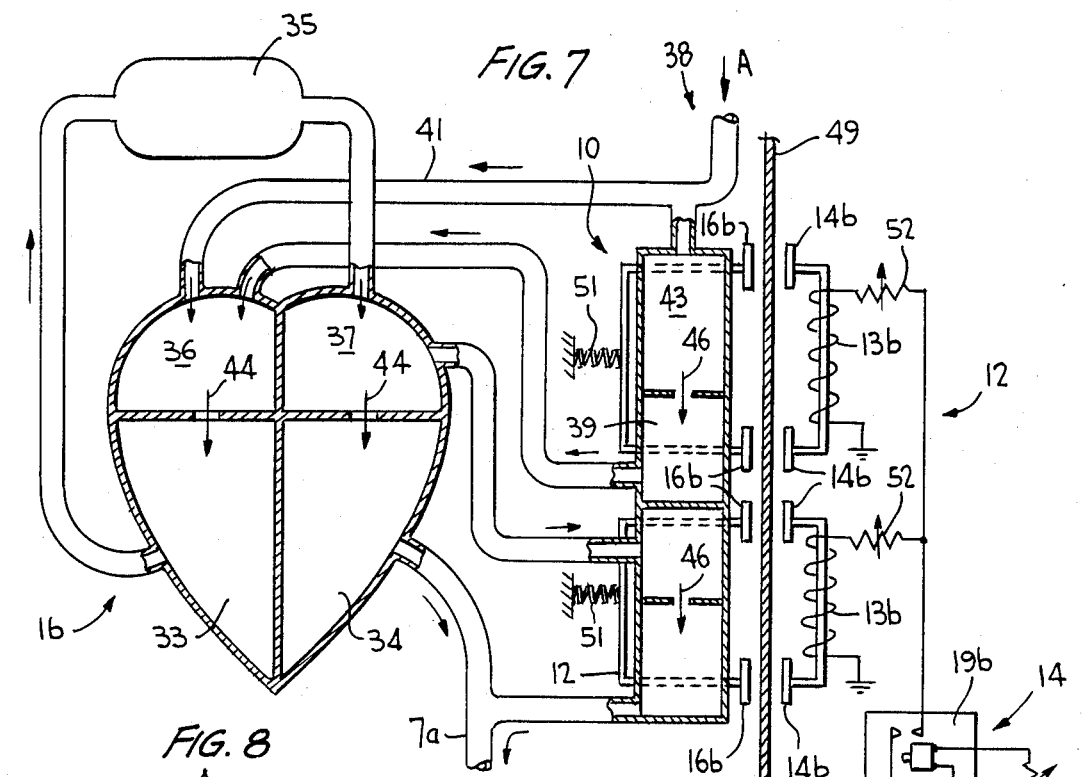
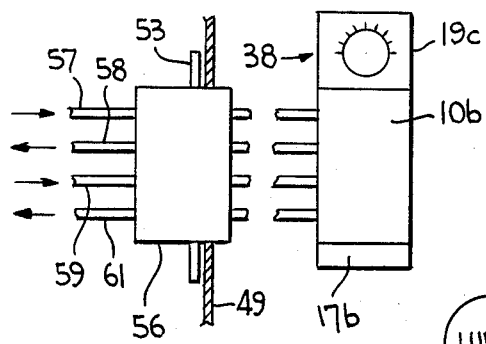
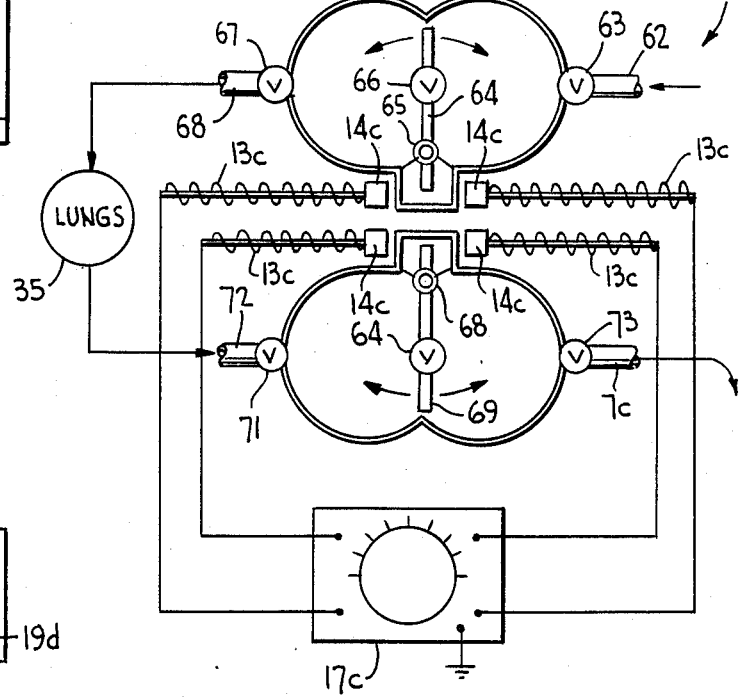
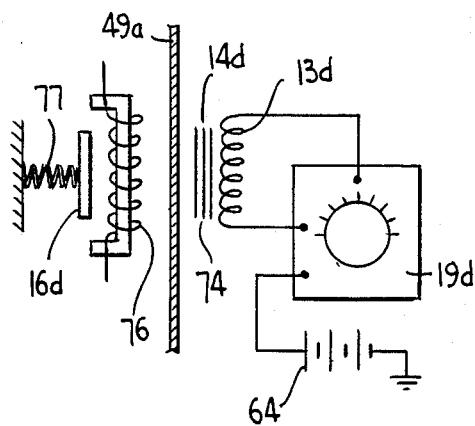

ELECTRO-MAGNETICALLY CONTROLLED ARTIFICIAL HEART DEVICE FOR COMPRESSING CARDIAC MUSCLE

BACKGROUND OF THE INVENTION

This invention relates to devices substituting for or assisting the heart, either corporally or extracorporally.

The blood supply to the heart muscle occurs via the coronary circulation. Defects in this area of the circulatory system are among the most common afflictions of mankind. When an increased amount of work is required of the heart, an increase in coronary blood flow must occur to provide for the additional oxygen requirements of the muscle fibers. The vessels in the coronary system differ from those in most of the rest of the body in that the major branches lie within contracting muscle fibers. External pressure by the myocardium during ventricular systole compresses the vessels and decreases blood flow, even though the aortic pressure is increased, 70 percent of the coronary arterial flow therefore occurs during diastole. Compression of the vessels, however, hastens the discharge of venous blood due to squeezing on the veins. Outflow from the coronary veins is therefore greater in systole than in diastole.

The left coronary artery supplies most of the left ventricle and the anterior portion of the ventricular septum. The right coronary artery supplies the right ventricle and the posterior portion of the septum. Since the left coronary artery supplies a large portion of the left ventricle, occlusion of a major branch generally seriously damages the pumping ability of this high pressure chamber. The right coronary arterial system on the other hand, supplies a chamber that needs to produce only low pressures and may suffer considerable damage without significant impairment of its pumping ability. Branches from the right coronary system supply the SA (sino-atrial) and AV (atrio-ventricular) nodal areas, however, and damage to these areas may produce life-threatening arrhythmias. In terms of relative flow distribution, about 85 percent of total coronary blood flow occurs through the left coronary artery and about 15 percent through the right coronary artery. Most of the venous return from the left coronary artery occurs through the great coronary vein into the coronary sinus in the right atrium; from the right coronary artery, venous return is via the anterior cardiac vein to the right atrium.

Cardiac muscle, like smooth muscle, skeletal muscle, and nerve, possesses a resting electrical potential relative to the ion distribution across the cell membrane. Like these tissues, it also has the ability to depolarize; depolarization (and repolarization) is manifested by a change in the electrical potential across the cell membrane. Most of the areas of the heart can depolarize spontaneously and thereby can contract without external nerve stimulation. This property of myocardial tissue is termed automaticity. Normally, the depolarization and repolarization processes proceed in an orderly fashion through the heart tissue, producing a characteristic electrocardiographic pattern. The SA node, a group of specialized muscle cells derived from the area of junction of the embryonic sinus venosus and the atrium, lies at the junction of the right atrium and the superior vena cava. These cells tend to depolarize spontaneously faster than those in any other area of the heart. Hence they normally control the heart rate and are called pacemaker cells. If for some reason this area fails to be the most rapidly depolarizing, the pacemaker site shifts to other areas, such as the AV node, which lies at the lower posterior, right side of the atrial septum and gives rise to a group of specialized muscle fibers.

All of these specialized muscle cells have the property of automaticity and serve to conduct the electrical impulse rapidly through the heart.

Once the cell potential reaches threshold, the characteristic rapid action potential is produced. This action potential spreads out from the SA node over the surface of the atria, activating the normally quiescent atrial cells. These cells in turn depolarize, and the impulse is thus passed to the AV nodal area. The specialized cells in the AV node repond poorly, and conduction through this area is very slow. In some cases the impulse may not get through at all, resulting in a dropped beat or a shift to another pacemaker site. Normally, however, after a short delay, the impulse spreads out to activate the ventricular muscle. The action potentials of the conduction bundles and ventricular muscle cells differ from those of the pacemaker and atrial areas in possessing a long plateau phase of depolarization. During this time the cell cannot be stimulated by another incoming action potential. This plateau phase lasts until the muscle contraction has been completed. Thus, unlike skeletal muscle, cardiac muscle cannot show tetanic contraction. This refractory abililty is important in the heart's action as a mechanical pump to allow adequate time for filling to occur.

Various abnormalities in the electrical activity of the heart resulting from damage to the SV or AV nodal areas are a primary cause of ineffectual contraction of the heart and subsequent death. Representative arrhythmias include a rapid, but regular, atrial rate (atrial tachycardia), which in some instances may be associated with a premature beat, before the normal diastolic time interval has passed, resulting in an earlier and usually less effective ventricular beat. In atrial flutter and atrial fibrillation the atrial rate is even more rapid. Flutter refers to a condition in which a rapid depolarization of the right atrium appears to occur in a circle around its junction with the superior and interior vanae cavae (circus depolarization); the resultant wave of electrical depolarization spreads out over the surface of the atria, causing rapid atrial contraction. Fibrillation refers to an even faster rate, in which there is not coordinated activity; rather, it appears that each small area of the muscle has a circus movement of its own, thereby producing no effectual contraction. In atrial fibrillation, the atrial rate is so fast that the ventricles respond at totally irregular times to an occasional impulse passing through the AV node.

The ventricular rate may not be the same as the atrial rate; i.e., the atrial beat may not be propagated through the AV node to the ventricle, or, contrariwise, the ventricle may initiate extra beats. If the beat originates in the ventricles, the resultant pattern of depolarization is abnormal. Ventricular premature beats or premature ventricular contractions (PVC's), are instances in which a single beat—or a short run of beats—occurs abnormally from a ventricular pacemaker site. If the ventricle is still in a depolarized state when the next atrial depolarization wave reaches it, there will be no response, and a compensatory pause will occur until the second normal atrial beat arrives. Rapidly firing ventricular sites produce ventricular tachycardia, an extremely dangerous condition, which may progress to ventricular fibrillation. In this condition no coordinated contraction occurs, and thus there is no effecting pumping of blood. This may be treated effectively only by electrically polarizing the entire heart muscle (defibrillating) and hoping to restart it from a single pacemaker site.

While advances in medical science have succeeded in counteracting some effects of such abnormalities, devices such as pacemakers have proved not entirely effective in regulating cardiac contractions, and are known in some instances to actually induce ventricular fibrillation. Further, heart transplants have had disappointing results, and are also extremely expensive.

SUMMARY OF THE INVENTION

This invention provides an artificial heart and/or a natural heart strengthening device, useful either corporally or extracorporally, comprising compressor means associated with a mammalian heart for compressing the cardiac muscle to simulate the normal pumping action thereof, and control means for electromagnetically controlling the operation of said compressor means.

It is accordingly an object of this invention to provide an artificial heart or heart strengthening device to simulate the natural heart pulsation of mammals by electromagnetic means which may operate alone or in conjunction with the natural heart.

It is a further object of this invention to provide an electromagnetized artificial heart including means for generating and controlling electromagnetic induction fields to induce pulsatory motion for pumping blood comparable to that of the natural mammalian heart.

It is an additional object of the invention to provide an artificial heart which controls ventricular fibrillation of the heart muscle by electromagnetic means.

It is yet another object of the invention to provide an artificial heart which is electrically-synchronized with the natural sino-auricular or auricular-ventricular nodal acitivity for concerted action of the natural and artificial hearts.

It is still further an object of this invention to provide an artificial heart which is simple and effective in alleviating the ravages of heart disease throughout the world.

It is still another object of this invention to provide an artificial heart which is flexible in operation.

BRIEF DESCRIPTION OF THE DRAWINGS

FIG. 3 is a view similar to that of FIG. 1 illustrating an alternate embodiment of the device of the invention;

FIG. 4 is a schematic illustration of a further embodiment of the device of the invention;

FIGS. 5 and 6 schematically illustrate exemplary control means and actuating means for the device of the invention;

FIG. 7 is a schematic illustration of the artificial heart of the invention;

FIG. 8 schematically represents the operating scheme of the artifical heart of FIG. 7;

FIG. 9 illustrates schematically an alternate embodiment of the artificial heart of FIG. 7; and FIG. 10 is a schematic illustration of an exemplary actuating means for the artificial heart of FIG. 9.

DETAILED DESCRIPTION OF THE INVENTION

Figure 1:
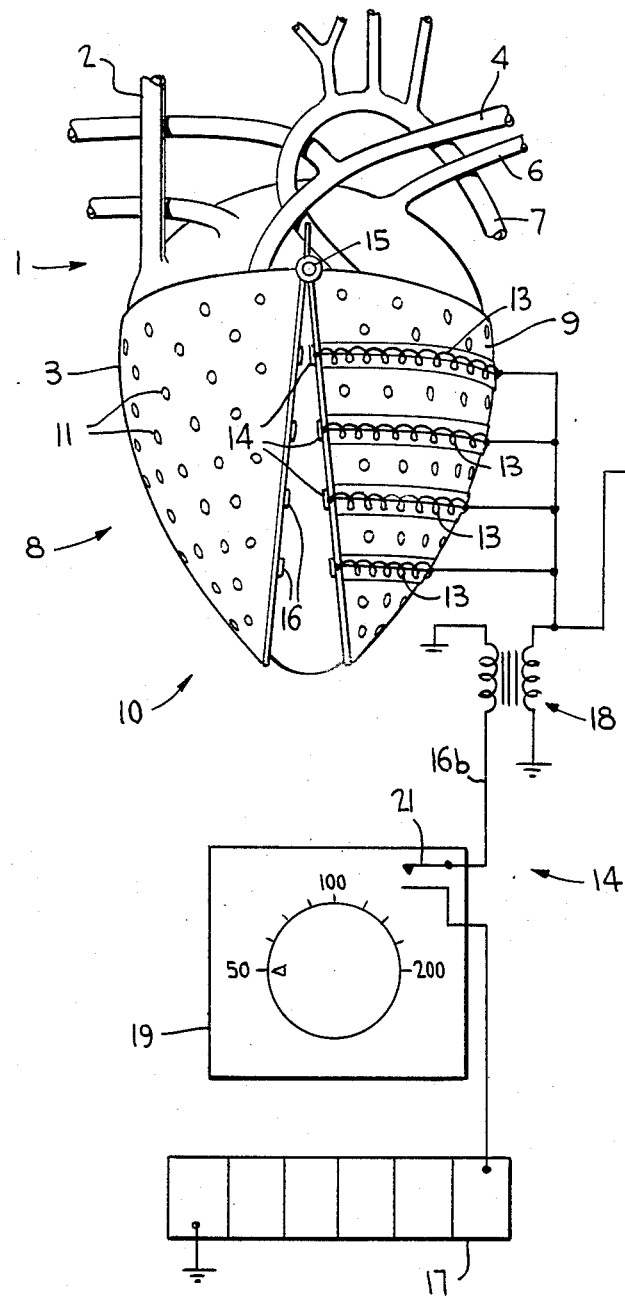
FIG. 1 is a perspective view of the artificial heart device of the invention.

With particular reference to FIG. 1, a mammalian heart compressing a cardiac muscle is schematically illustrated at 1, showing the associated major coronary vessels compressing the superior vena cava 2, the inferior vena cava 3, the pulmonary artery 4, the pulmonary vein 6 and the aorta 7 and other vessels (not designated). The artificial heart device of the invention, generally designated at 8, is shown in association with the heart 1. The device 8 includes compressor means generally indicated at 10 for compressing the cardiac muscle 1 to simulate normal pumping action of this muscle, comprising first and second compressor components 9 and 11 disposed on the surface of the heart 1 and conforming to the contours thereof. The components 9 and 10 are disposed so that they are in spaced relationship as shown, when the heart 1 is relaxed, or in a rest mode and so that they are in mating relationship when the heart 1 is in a pumping mode (contracted); preferably the components 9 and 10 are pivotally joined, as by a hinge 15. In the illustrated embodiment, the components 9 and 10 are fabricated from sheets of a metal such as steel, gold, or platinum, perforated to reduce the weight thereof, or stainless steel net. Alternate materials include biocompatible-plastics such as polyurethane, silicone or natural or synthetic rubber, optionally impregnated with particles of a ferrous metal or an alloy thereof.

Figure 2:
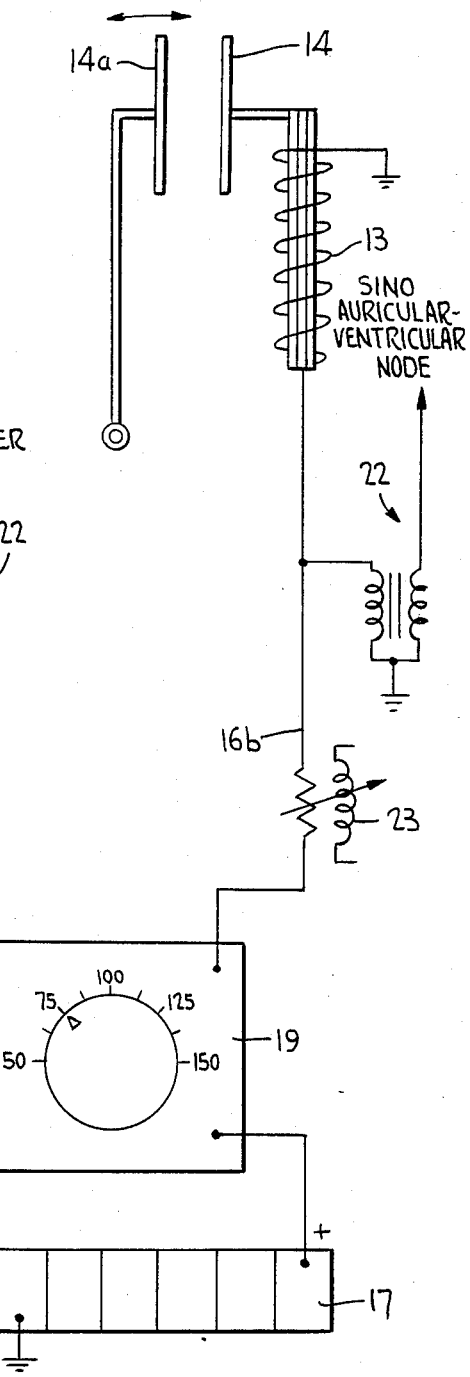
FIG. 2 is a schematic diagram of the artificial heart of FIG. 1.

The device 8 further includes control means generally indicated at 12 for electromagnetically controlling the operation of compressor means 10, comprising a plurality of electromagnets 13 disposed on compressor component 9. Each electromagnet 13 includes an active pole element 14 disposed for electromagnetic interaction with a corresponding passive pole element 16 disposed on second compressor component 11 when the electromagnets 13 are actuated. Actuating means generally indicated at 14 for actuating the electromagnets 13 comprises an electrical circuit 16 including a power generator such as a rechargeable battery 17 and a transformer 18 for regulating the amount of power and current supplied to the electromagnets 13 by the battery 17. Preferably, the circuit 16 further includes vibratory means such as a vibrator 19 for regulating the actuations of the electromagnets 13 to provide a pulsating current in the circuit 16 of, for example, 50 to 200 pulses per minute to correspond with the natural pulsations of the heart 1. The vibrator 19, or other electric vibratory means similar to an electric door bell condenser and battery arrangement, such as a rotary motor having suitable distribution contacts or an alternating vibratory current or vibratory unit, is controlled by an on/off switching mechanism 21. The device 8 may further include means generally indicated at 22 for triggering the SA or AV nodal activity of the heart 1. The device 8 of FIG. 1 is schematically illustrated in FIG. 2, further including a coil delay unit 23. An exemplary supporting system for supporting the device 8 within the mammalian body is illustrated in FIG. 3, comprising a supportive loop 24 secured to ribs 26 and carrying spring-loaded hinges 15a pivotally connecting compressor components 9 and 10, an biasing them in the resting mode illustrated. The compressor components or shrouds 9 and 10 may, in an alternate embodiment (not illustrated) be divided into four segments adjacent or alternating with the active or passive pole elements 14 or 16, respectively; the segments may, if desired, be associated only with the ventricular portions of the heart 1.

In operation, the switching mechanism 21 is activated, and current is generated by the battery 17 and supplied to the electromagnets 13 as regulated by the vibrator 19. As the electromagnets 13 are energized, the associated active pole elements 14 are activated, attracting corresponding pole elements 16. The compressor components 9 and 11 are thus pivotally drawn together on hinge 15 to thereby compress the heart 1 and force blood through the associated vessels 2-7 in a rhythm according to the pulsating current supplied through the circuit 16. When the switch 21 is turned off, the electromagnets 13 are de-activated, and the heart 1 returns to the normal position illustrated in FIG. 1 by its natural resilience optionally assisted by hinges 15a (FIG. 3) spring biasing components 9 and 11 into spaced relationship. The action of components 9 and 11 are optionally synchronized with the natural SA and AV nodal rhythms of the heart 1 by current supplied by vibrator 19 to the triggering mechanism 22 simultaneously with the actuation of electromagnets 13.

In an alternate embodiment of the invention illustrated in FIG. 4, an electromagnet 13a is disposed outside the mammalian body, partially defined by body wall 26. On actuation of the electromagnet 13a, associated active pole elements 14a are activated to attract passive pole elements 16a and operate compressor component 11a to compress the heart 1a. On de-actuation of the electromagnet 13a, the component 11a is returned to open position as by spring 27 biasing the component 11a in open position, as illustrated. The embodiment illustrated is particularly effective in controlling ventricular fibrillation by compression of the heart 1 by actuation of the electromagnet 13a at a predetermined rate to eliminate the fibrillation. This is accomplished by sequential activation of the vibrator (not shown) regulating current to the electromagnet 13a. FIGS. 5 and 6 illustrate schematically the control means 12 and actuating means 14 for the device 8 described supra in connection with FIGS. 1-4. In the embodiment of FIG. 5, numeral 28 designates a battery-operated small rotary motor for switching the electromagnets 13 on or off by its rotary motion through contacts 29 associated with mounting means 31. FIG. 6 illustrates schematically control and actuating means 12 and 14, respectively, useful in connection with the embodiment illustrated in FIG. 4.

In a further embodiment of the invention, FIG. 7 illustrates an artificial heart incorporating the compressor means 10, control means 12, and actuating means 14 of the previous embodiments, here disposed, however, outside the mammalian body.

Referring to FIG. 7 in detail schematically illustrated is a pair of lungs 35 and a heart 1b including right and left ventricles 33 and 34 respectively; right and left atria 36 and 37 respectively; and an aorta 7a. Also schematically illustrated is an artificial heart generally indicated at 38, including right and left ventricles 39 and 41, respectively; and right and left atria 42 and 43 respectively. The artificial heart 38 further includes control valve 44 and 46 for controlling the flow of blood between natural heart 1b and artificial heart 38.

The arrows indicate the flow of blood controlled by valves 44 and 46 through the natural and artificial hearts 1b and 38 brought about by electromagnets 13b and pole elements 14b by the magnetic attraction of pole elements 16b. Artificial heart 38 further includes connecting elements 47 and 48 between the pole elements 14b and 16b. A body wall 49 separates heart 16b and 38.

The mechanism of the artificial heart is operated by a vibratory unit 19b which operates the electromagnets 13b provided with pole elements 14b. A coil delay unit 23a controls the frequency of the vibratory movement and provides synchronism with the natural heart pulsations via switches 52 at, for example, 70 to 100 beats per minute.

It is apparent that when electromagnets 13b are energized by the vibratory unit 19b, they attact pole elements 16b and when de-energized, the artificial heart 38 will return to its normal position due to its natural resilience assisted by biasing springs 51. Pole elements 16b may project outside the body of the animal, for example, by creating a non-leakable arrangement by surrounding the horizonal parts of connecting elements 47 and 48 supporting the pole elements, by a pole (not shown).

Thus, a rhythmic beat is created in unison with the natural heart 1b. The letter "A" represents used blood from the body, and the letter "Z" indicates fresh blood supply to the body.

FIG. 8 schematically illustrates the operating scheme of FIG. 7, wherein the heart 38 is placed outside the mammal's body. The numeral 49 represents the body wall and numeral 53 the artifical metal or plastic platform supported by the ribs and the animal's body on which is mounted a plug 56 with a channel 57 for receiving blood from the body; a channel 58 for transferring it to the lungs (not shown); a channel 59 for transporting blood from the lungs to the left ventricle (not shown); and a channel 61 for transference of the blood to the aorta (not shown).

Outside the body are situated corresponding channels to the compressor means 10b. Also shown is the regulating vibrator 19c for activating or switching off the compressor 10b. Numeral 17b represents a battery, eliminator, or rechargeable battery for supplying the appropriate power for the operation of the artificial heart 38.

FIG. 9 illustrates a similar artificial heart 38b. A channel 62 equipped with a control valve 63 receives blood from the body; a diaphragm 64 is fitted with a valve 66; 65 is the fulcrum of diaphragm 64. A valve 67 controls blood being pumped to the lungs 35; and channel 68 supplies blood to the lungs 35. As the electromagnets 13c are energized from vibrator 17c, the pole elements 14c become magnets and attract diaphragms or extensions 64 and 69 alternately; the movement of the diaphragms 64 and 69 is indicated by the arrows.

Similarly, blood received from the lungs 35 at 72 is forced by diaphragm 69 including valve 64, and assisted by controlling valve 71; 68 represents the fulcrum of diaphragm 69. The movement of the diaphragm 69 is indicated by arrows as it is actuated by electromagnets 13c and pole elements 14c. The blood is thus pumped to the aortas 7c and controlled by valve 73.

FIG. 10 is a power supply diagram illustrating the electrical power supplied to vibrator 19d, which can be adjusted to vibrate at frequencies ranging from about 50 to 200.

The power supply system illustrated includes a coil 74, an electromagnetic coil 76 and pole elements 14d which alternately attract movable pole elements 16d coupled to a spring 77, which may be replaced by an electromagnet 13d. In this embodiment, the numeral 49a represents the body wall.

Various components outside the body may be enclosed in a suitably shaped container provided with several vacuum cups to hold it in position assisted by a brassiere or a holster.

Body tissues may be rendered capable of being attracted to a magnet by superimposing stainless steel gauze or a thin stainless steel plate by a surgical operation, or by depositing very fine stainless steel filings inside the animal tissue by projecting them from an injector gun.

It is apparent that the natural and artificial hearts 1 and 38 may be used in conjunction with one another, or singly operated by control means 12 described supra.

I claim:

1. An artificial heart device comprising compressor means adapted to be associated with a mammalian heart for compressing the cardiac muscle to stimulate the normal pumping action thereof, and control means for electromagnetically controlling the operation of said compressor means, said compressor means comprising a pair of first and second compressor components adapted to be disposed on the surface of the heart in spaced relationship for electromagnetic interaction to compress said cardiac muscle on actuation of said control means, wherein the first compressor component includes a set of pole elements disposed for electromagnetic interaction with a set of corresponding pole elements on the second compressor component.

2. The invention of claim 1, wherein at least said compressor means are adapted to be juxtaposed with said heart muscle.

3. The invention of claim 1, wherein said control means functions to synchronize the action of said compressor means with the atrial and ventricular rhythmic contractions of the normal heart.

4. The invention of claim 1, wherein each of said components comprises a metal sheet conforming to a portion of the surface of said heart muscle.

5. The invention of claim 1, wherein the electromagnetic actuation of said pole elements is regulated by vibratory means for producing rhythmatic electromagnetic interaction of said pole elements to compress said cardiac muscle synchronistically with its normal pumping action.

* * * * *